(12) United States Patent
Finn et al.

(10) Patent No.: US 9,522,188 B2
(45) Date of Patent: Dec. 20, 2016

(54) ABUSE RESISTANT TRANSMUCOSAL DRUG DELIVERY DEVICE

(75) Inventors: Andrew Finn, Raleigh, NC (US); Niraj Vasisht, Cary, NC (US)

(73) Assignee: BioDelivery Sciences International, Inc., Raleigh, NC (US)

( * ) Notice: Subject to any disclaimer, the term of this patent is extended or adjusted under 35 U.S.C. 154(b) by 3054 days.

(21) Appl. No.: 11/639,408

(22) Filed: Dec. 13, 2006

(65) Prior Publication Data

US 2007/0148097 A1 Jun. 28, 2007

Related U.S. Application Data

(60) Provisional application No. 60/750,191, filed on Dec. 13, 2005, provisional application No. 60/764,619, filed on Feb. 2, 2006.

(51) Int. Cl.
| | |
|---|---|
| *A61K 31/485* | (2006.01) |
| *A61K 45/06* | (2006.01) |
| *A61K 9/00* | (2006.01) |
| *A61K 9/70* | (2006.01) |
| *A61K 31/4468* | (2006.01) |

(52) U.S. Cl.
CPC ............... *A61K 45/06* (2013.01); *A61K 9/006* (2013.01); *A61K 9/0014* (2013.01); *A61K 9/7007* (2013.01); *A61K 9/7038* (2013.01); *A61K 9/7092* (2013.01); *A61K 31/4468* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 4,582,835 A | 4/1986 | Lewis et al. | |
| 5,149,538 A | 9/1992 | Granger et al. | |
| 5,236,714 A | 8/1993 | Lee et al. | |
| 6,200,604 B1 | 3/2001 | Pather et al. | |
| 6,228,863 B1 | 5/2001 | Palermo et al. | |
| 6,277,384 B1 | 8/2001 | Kaiko et al. | |
| 6,375,957 B1 | 4/2002 | Kaiko et al. | |
| 6,475,494 B2 | 11/2002 | Kaiko et al. | |
| 6,562,363 B1 | 5/2003 | Mantelle et al. | |
| 6,582,724 B2 | 6/2003 | Mantelle et al. | |
| 6,696,066 B2 | 2/2004 | Kaiko et al. | |
| 6,696,088 B2 | 2/2004 | Oshlack et al. | |
| 6,716,449 B2 | 4/2004 | Oshlack et al. | |
| 6,719,997 B2 | 4/2004 | Hsu et al. | |
| 6,759,059 B1 | 7/2004 | Pettersson et al. | |
| 6,835,392 B2 | 12/2004 | Hsu et al. | |
| 6,969,374 B2 | 11/2005 | Krantz et al. | |
| 7,144,587 B2 | 12/2006 | Oshlack et al. | |
| 7,157,103 B2 | 1/2007 | Sackler | |
| 7,172,767 B2 | 2/2007 | Kaiko et al. | |
| 2002/0034554 A1 | 3/2002 | Hsu et al. | |
| 2002/0058068 A1 | 5/2002 | Houze et al. | |
| 2002/0160043 A1 | 10/2002 | Coleman | |
| 2003/0044446 A1* | 3/2003 | Moro et al. | 424/426 |
| 2003/0104041 A1 | 6/2003 | Hsu et al. | |
| 2003/0124176 A1 | 7/2003 | Hsu et al. | |
| 2003/0161870 A1 | 8/2003 | Hsu et al. | |
| 2003/0170195 A1 | 9/2003 | Houze et al. | |
| 2003/0194420 A1 | 10/2003 | Holl et al. | |
| 2004/0018241 A1 | 1/2004 | Houze et al. | |
| 2004/0024003 A1 | 2/2004 | Asmussen et al. | |
| 2004/0033255 A1 | 2/2004 | Baker et al. | |
| 2004/0110781 A1 | 6/2004 | Harmon et al. | |
| 2004/0126323 A1 | 7/2004 | Shevchuk et al. | |
| 2004/0126416 A1 | 7/2004 | Reidenberg et al. | |
| 2004/0151774 A1 | 8/2004 | Pauletti et al. | |
| 2004/0191301 A1 | 9/2004 | Van Duren | |
| 2004/0213828 A1 | 10/2004 | Smith | |
| 2004/0219195 A1 | 11/2004 | Hart et al. | |
| 2004/0219196 A1 | 11/2004 | Hart et al. | |
| 2004/0220262 A1 | 11/2004 | Hsu et al. | |

(Continued)

FOREIGN PATENT DOCUMENTS

| | | |
|---|---|---|
| EP | 1021204 B1 | 7/2000 |
| EP | 1105104 B1 | 6/2001 |
| EP | 1201233 B1 | 5/2002 |
| WO | WO-98/26780 | 6/1998 |
| WO | WO-01/58447 A1 | 8/2001 |
| WO | WO-01/85257 A2 | 11/2001 |
| WO | WO-02/092060 A1 | 11/2002 |
| WO | WO-03/013525 A1 | 2/2003 |
| WO | WO-03/013538 A1 | 2/2003 |
| WO | WO-03/070191 A1 | 8/2003 |
| WO | WO-2004/017941 A2 | 3/2004 |
| WO | WO 2004017941 A2 * | 3/2004 |
| WO | WO-2005/044243 A2 | 5/2005 |
| WO | WO-2005/055981 A2 | 6/2005 |
| WO | WO-2005/081825 A2 | 9/2005 |

OTHER PUBLICATIONS

Katz, Nathaniel, P. et al., "Anesthetic and Life Support Drugs Advisory Committee, Meeting, Wednesday, Jan. 2002," retrieved onine at http://www.fda.gov/ohrms/dockets/ac/02/transcripts/3820t1.pdf (2002).

(Continued)

*Primary Examiner* — Michael G Hartley
*Assistant Examiner* — Nabila Ebrahim
(74) *Attorney, Agent, or Firm* — McCarter & English, LLP; Danielle L. Herritt; Wei Song

(57) ABSTRACT

The present invention relates to a solid pharmaceutical dosage form for abusable drug delivery with reduced illicit abuse potential. The dosage form is presented as a bioerodable transmucosal delivery device that includes an abusable drug and an antagonist to the abusable drug associated with an abuse-resistant matrix. The devices of the invention may be in the form of a layered film or a tablet. Upon application in a non-abusive manner, the device adheres to the mucosal surface, providing transmucosal drug delivery of the drug with minimal absorption of the antagonist into systemic circulation.

21 Claims, 1 Drawing Sheet

(56) References Cited

U.S. PATENT DOCUMENTS

| | | |
|---|---|---|
| 2004/0241218 A1 | 12/2004 | Tavares et al. |
| 2005/0002997 A1 | 1/2005 | Howard et al. |
| 2005/0013845 A1 | 1/2005 | Warren et al. |
| 2005/0042281 A1 | 2/2005 | Singh et al. |
| 2005/0074487 A1 | 4/2005 | Hsu et al. |
| 2005/0095279 A1* | 5/2005 | Gale et al. .................. 424/449 |
| 2005/0169977 A1 | 8/2005 | Kanios et al. |
| 2005/0222135 A1 | 10/2005 | Bushmann et al. |
| 2006/0003008 A1 | 1/2006 | Gibson et al. |
| 2006/0069086 A1 | 3/2006 | Michalow |
| 2006/0073102 A1 | 4/2006 | Huaihung et al. |
| 2006/0130828 A1 | 6/2006 | Sexton et al. |

OTHER PUBLICATIONS

1999 Refresher Course Lecture and Clinical Update Index, retrieved online at http://anesthesia.stanford.edu/RCLS.pdf (1999).

Lahmeyer, H.W. et al., "Pentazocine-naloxone: an 'abuse proof' drug can be abused," *J. Clin. Psychopharmacol.*, vol. 6(6):389-390 (1986).

U.S. Department of Justice, "Intelligence Bulletin, Buprenorphine: Potential for Abuse," retrieved online at http://www.usdoj.gov/ndic/pubs10/10123/10123p.pdf.

International Search Report for Appliation No. PCT/US2006/047686, dated Aug. 13, 2007.

\* cited by examiner

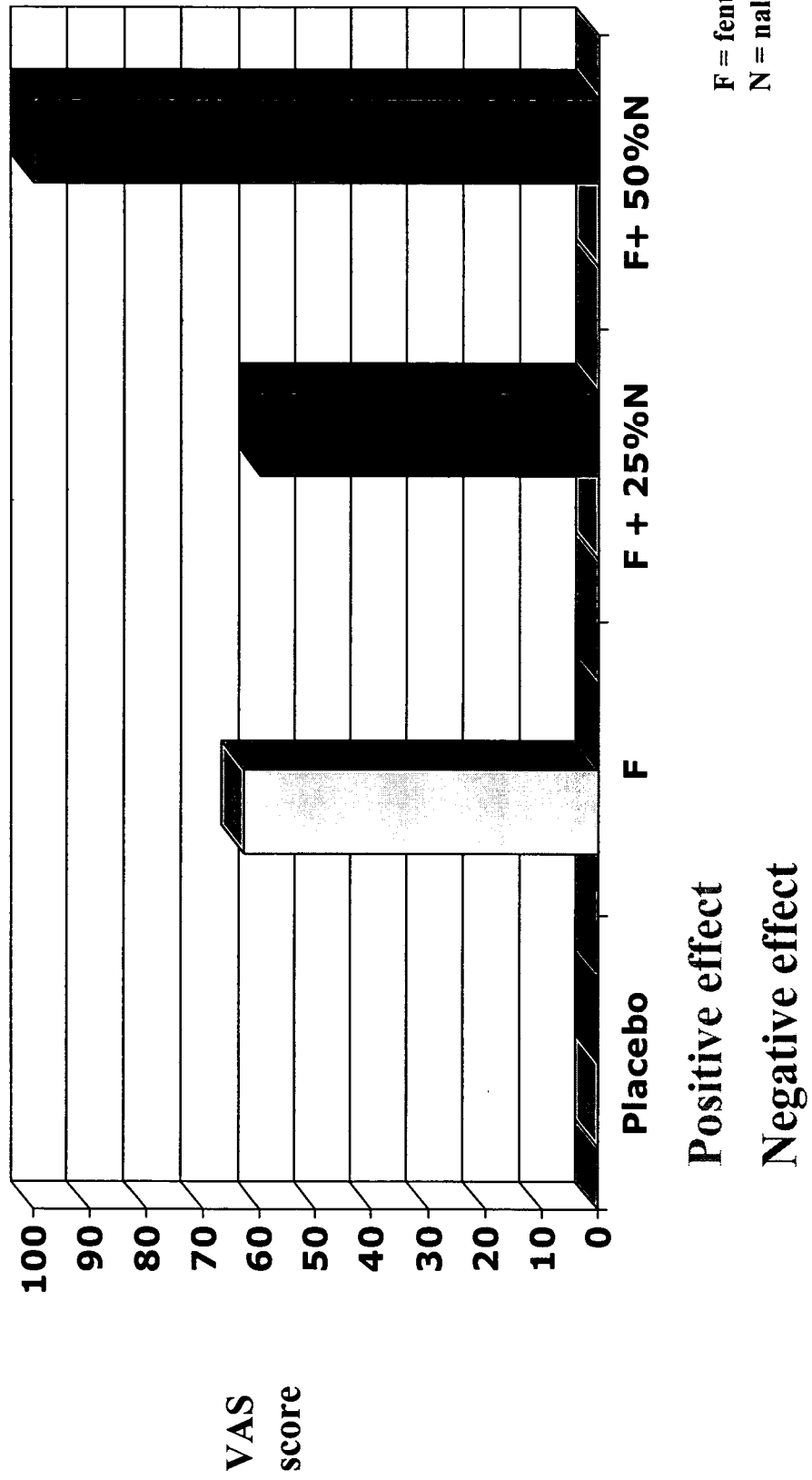

ABUSE RESISTANT TRANSMUCOSAL DRUG DELIVERY DEVICE

RELATED APPLICATIONS

This application claims the benefit of and priority to U.S. Provisional Application No. 60/750,191, filed on Dec. 13, 2005 and U.S. Provisional Application No. 60/764,619, filed on Feb. 2, 2006. The contents of these applications are hereby incorporated by this reference in their entireties.

BACKGROUND OF THE INVENTION

Opioids, or opioid agonists, refer generally to a group of drugs that exhibit opium or morphine-like properties. Opioids can be employed as moderate to strong analgesics, but have other pharmacological effects as well, including drowsiness, respiratory depression, changes in mood and mental clouding without a resulting loss of consciousness. Opium contains more than twenty distinct alkaloids. Morphine, codeine and papaverine are included in this group. With the advent of totally synthetic entities with morphine-like actions, the term "opioid" was generally retained as a generic designation for all exogenous substances that bind stereo-specifically to any of several subspecies of opioid receptors and produce agonist actions.

The potential for the development of tolerance and physical dependence with repeated opioid use is a characteristic feature of all the opioid drugs, and the possibility of developing psychological dependence (i.e., addiction) is one of the major concerns in the treatment of pain with opioids. Another major concern associated with the use of opioids is the diversion of these drugs from the patient in pain to another (non-patient) for recreational purposes, e.g., to an addict.

While opioids are highly successful in relieving and preventing moderate to severe pain, they are subject to abuse to achieve a state of narcosis or euphoria. Oral intake of such drugs by abusers, however, does not usually give rise to the euphoric result desired by the abuser, even when taken in an abusively large quantity, because of poor uptake of such drugs through the GI tract.

Because a particular dose of an opioid analgesic is typically more potent when administered parenterally as compared to the same dose administered orally, one mode of abuse of oral medications involves the extraction of the opioid from the dosage form, and the subsequent injection of the opioid (using any suitable vehicle for injection) in order to achieve a "high." Such extraction is generally as easy as dissolving the dosage form using an aqueous liquid or a suitable solvent. Oral opioid formulations, however, are not only being abused by the parenteral route, but also via the oral route when the patient or addict orally self-administers more than the prescribed oral dose during any dosage interval. In another mode of abuse, the corresponding dosage forms are comminuted, for example ground, by the abuser and administered, for example, by inhalation. In still another form of abuse, the opioid is extracted from the powder obtained by comminution of the dosage form (optionally dissolving in a suitable liquid) and inhaling the (dissolved or powdered) opioid. These forms of administration give rise to an accelerated rise in levels of the abusable drug, relative to oral administration, providing the abuser with the desired result.

Some progress has been made in the attempt to alleviate or lessen the problem of opioid abuse. For example, U.S. Pat. No. 5,866,164 proposes an oral osmotic therapeutic system with a two-layer core, wherein the first layer of the core, facing towards the opening of the system comprises an opioid analgesic and the second layer comprises an antagonist for this opioid analgesic and simultaneously effects the push function, i.e., expelling the analgesic from the corresponding layer out of the opening of the system. U.S. Pat. No. 6,228,863 describes an oral dosage form containing a combination of an opioid agonist and an opioid antagonist, the formulation of which has been selected such that the two compounds can in each case only be extracted together from the dosage form and then an at least two-stage process is required to separate them.

U.S. Pat. No. 4,582,835 describes a method of treating pain by administering a sublingually effective dose of buprenorphine with naloxone. U.S. Pat. No. 6,277,384 also discloses a dosage form containing a combination of an opioid agonist and an opioid antagonist in a specific ratio that brings about a negative effect on administration to an addicted person. U.S. Application Publication No. 2004/0241218 discloses a transdermal system which includes an inactivating agent, e.g., a substance which crosslinks the opioid drug, to prevent abuse. Such transdermal formulations may also include an antagonist.

SUMMARY OF THE INVENTION

The present invention provides a bioerodable abuse resistant transmucosal drug delivery device and method of treatment using such devices. The drug delivery devices of the present invention provide reduced illicit abuse potential and are particularly useful in, e.g., opioid transmucosal drug delivery. The transmucosal drug delivery devices of the present invention generally include a drug and its antagonist contained within the device such that abuse of the drug is impeded.

Thus, for example, illicit use efforts to extract an abusable drug from the transmucosal devices of the present invention for parenteral injection (e.g., by extraction of the drug by dissolving some or all of the transmucosal device in water or other solvent), are thwarted by the co-extraction of an antagonist. The amount of antagonist contained in the product is chosen to block any psychopharmacological effects that would be expected from parenteral administration of the drug alone. The antagonist is generally associated with an abuse-resistant matrix, and does not interfere with the transmucosal delivery of the drug.

One of the advantages of the devices of the present invention is that the devices generally include an abuse-resistant matrix that does not effectively release the antagonist when the device is used in a non-abusive manner. The dosage forms described in U.S. Pat. No. 4,582,384 and U.S. Pat. No. 6,227,384, even when correctly administered, release the corresponding antagonist into the mucosa along with the opioid. This impairs the activity of the opioid analgesic and it often becomes necessary to increase the quantity thereof required in the dosage form for satisfactory treatment of the patient. The risk of the occurrence of undesirable accompanying symptoms is also increased in comparison to dosage forms which contain no opioid antagonists. Moreover, it is desirable not to further increase the stress on the patient by releasing a large proportion of opioid antagonist when such a dosage form is correctly administered.

One of the advantages of the devices of the present invention is that the devices are bioerodable, such that the devices do not have to be removed after use.

Accordingly, in one aspect, the present invention includes a bioerodable abuse-resistant drug delivery device. The device generally includes transmucosal drug delivery composition and an abuse-resistant matrix. The transmucosal drug delivery composition includes an abusable drug and the abuse-resistant matrix includes an antagonist to the abusable drug. The delivery device can be, for example, a mucoadhesive drug delivery device, a buccal delivery device, and/or a sublingual delivery device. In some embodiments, the antagonist is substantially transmucosally unavailable. In other embodiments, the device is substantially free of inactivating agents.

In some embodiments, the abuse-resistant matrix is a layer or coating, e.g., a water-erodable coating or layer at least partially disposed about the antagonist. In some embodiments, the abuse-resistant matrix is a water-hydrolysable, water-erodable or water-soluble matrix, e.g., an ion exchange polymer. In some embodiments, the delivery device is in the form of a tablet, a lozenge, a film, a disc, a capsule or a mixture of polymers.

In some embodiments, the device includes a mucoadhesive layer. In some embodiments, the device includes a mucoadhesive layer and a non-adhesive backing layer. In other embodiments, the device includes a third layer disposed between the mucoadhesive layer and the backing layer. In some embodiments, either or both of the abusable drug and the abuse-resistant matrix are incorporated into a mucoadhesive layer. In some embodiments, the abuse-resistant matrix is incorporated into the backing layer. In some embodiments, either or both of the abusable drug and the abuse-resistant matrix are incorporated into the third layer. In some embodiments, the abuse-resistant matrix is the third layer. In some embodiments, either or both of the abusable drug and the abuse-resistant matrix are incorporated into any combination of layers discussed herein. In some embodiments, the abusable drug is incorporated into the mucoadhesive layer and the abuse-resistant matrix is incorporated into the backing layer.

In some embodiments, the abuse-resistant matrix erodes at a slower rate than the backing layer, the mucoadhesive layer, the third layer, or any combination thereof.

In some embodiments, the abusable drug can be, but is not limited to opiates and opioids, e.g., alfentanil, allylprodine, alphaprodine, apomorphine, anileridine, apocodeine, benzylmorphine, bezitramide, buprenorphine, butorphanol, clonitazene, codeine, cyclorphan, cyprenorphine, desomorphine, dextromoramide, dextropropoxyphene, dezocine, diampromide, diamorphone, dihydrocodeine, dihydromorphine, dimenoxadol, eptazocine, ethylmorphine, etonitazene, etorphine, fentanyl, fencamfamine, fenethylline, hydrocodone, hydromorphone, hydroxymethylmorphinan, hydroxypethidine, isomethadone, levomethadone, levophenacylmorphan, levorphanol, lofentanil, mazindol, meperidine, metazocine, methadone, methylmorphine, modafinil, morphine, nalbuphene, necomorphine, normethadone, normorphine, opium, oxycodone, oxymorphone, pholcodine, profadol remifentanil, sufentanil, tramadol, corresponding derivatives, physiologically acceptable compounds, salts and bases.

In some embodiments, the antagonist includes, but is not limited to opiate or opioid antagonists, e.g., naloxone, naltrexone, nalmefene, nalide, nalmexone, nalorphine, naluphine, cyclazocine, levallorphan and physiologically acceptable salts and solvates thereof.

In some embodiments, the abuse-resistant matrix includes, but is not limited to, partially crosslinked polyacrylic acid, Polycarbophil™, Providone™, cross-linked sodium carboxymethylcellulose, gelatin, chitosan, Amberlite™ IRP69, Duolite™ AP143, AMBERLITE™ IRP64, AMBERLITE™ IRP88, and combinations thereof. In other embodiments, the abuse-resistant matrix includes, but is not limited to, alginates, polyethylene oxide, poly ethylene glycols, polylactide, polyglycolide, lactide-glycolide copolymers, poly-epsilon-caprolactone, polyorthoesters, polyanhydrides and derivatives, methyl cellulose, ethyl cellulose, hydroxypropyl cellulose, hydroxyethyl cellulose, hydroxyethylmethyl cellulose, hydroxypropylmethyl cellulose, polyacrylic acid, and sodium carboxymethyl cellulose, poly vinyl acetate, poly vinyl alcohols, polyethylene glycol, polyethylene oxide, ethylene oxide-propylene oxide copolymers, collagen and derivatives, gelatin, albumin, polyaminoacids and derivatives, polyphosphazenes, polysaccharides and derivatives, chitin, or chitosan bioadhesive polymers, polyacrylic acid, polyvinyl pyrrolidone, sodium carboxymethyl cellulose, and combinations thereof.

In some embodiments, the device is less susceptible to abuse than an abusable drug alone. In other embodiments, less than 30% of the efficacy of the abusable drug is retained when used in an abusive manner. In some embodiments, the antagonist and the abusable drug are released at substantially the same rate when abusively dissolved. In some embodiments, the antagonist and the abusable drug are released at substantially the same rate when dissolved in water. In other embodiments, the ratio of released antagonist to released abusable drug is not less than about 1:20.

In some aspects, the present invention provides a method for treating pain in a subject. The method includes administering any device described herein such that pain is treated. In some embodiments, the extent of the absorption into systemic circulation of the antagonist by the subject is less than about 15% by weight. In some embodiments, the dosage of the abusable drug is between about 50 µg and about 10 mg.

In some aspects, the bioerodable abuse-resistant drug delivery device comprising: a layered film having at least one bioerodable, mucoadhesive layer to be placed in contact with a mucosal surface, and at least one bioerodable non-adhesive backing layer, wherein at least one abusable drug is incorporated in at least the mucoadhesive layer, and an abuse-resistant matrix comprising an antagonist to the abusable drug is incorporated in any or all of the layers.

BRIEF DESCRIPTION OF THE FIGURES

FIG. 1 graphically depicts the measure of positive and negative effects felt by a subject who was administered placebo, fentanyl only, and varying ratios of fentanyl and naloxone.

DETAILED DESCRIPTION OF THE INVENTION

Subjects with pain, e.g., cancer pain, are typically opioid tolerant because of the chronic narcotic use required to control such pain. Moreover, the dose of transmucosal opioid drug, e.g., fentanyl, required to treat breakthrough pain (for example, pain associated with unusual movement) can be high because of the opioid tolerance. In fact, doses in excess of one mg, a dose that would be fatal for a subject that was not opioid tolerant, are often used. This amount of a potent narcotic in a device makes it potentially subject to diversion and abuse by the intended route of administration as well as through extraction of the fentanyl for injection or inhalation.

Abuse by injection can be prevented or reduced by the inclusion of an antagonist, such as naloxone, in the formulation, which would block any psychopharmacologic effect of injected opioid drug.

Accordingly, the present invention relates to novel drug delivery devices that provide for the transmucosal delivery of an abusable drug while reducing, and, in some embodiments, eliminating abuse potential. The drug delivery devices generally include an abusable drug and at least one antagonist for the drug incorporated into a device (e.g., a multilayered transmucosal delivery device) that impedes abuse of the drug. Abuse of the drug can be impeded by use of the present invention in many, non-limiting ways. In some embodiments, the antagonist impedes abuse of the drug because attempts to extract the drug from the transmucosal delivery device results in co-extraction of the antagonist which blocks the expected effect of the drug. In other embodiments, the abusable drug and the antagonist are incorporated into the same layer or indistinguishable layers of a delivery device of the present invention, so that they can not be separated from one another, e.g., by peeling one layer off of the device.

When used as intended, however, the abusable drug will be delivered through the mucosa, e.g., by application to the mucous membrane of the mouth, and thus into the systemic circulation. The antagonist is associated with an abuse-resistant matrix, e.g., dispersed within coated-microparticles or chemically-bound to a polymer that impedes or prevents mucoabsorption, e.g., a high molecular weight polymer or an ion exchange polymer. In some embodiments, the antagonist is substantially transmucosally unavailable when used in a non-abusive manner. Without wishing to be bound by any particular theory, it is believed that when used in a non-abusive manner, the opioid antagonist will be swallowed, e.g., as an unbound antagonist in a layer or matrix not contacting the mucosa and/or as an intact microcapsule, polymer bound particle or in some other form not amenable to mucosal administration. Because the opioid antagonist is poorly absorbed from the gastrointestinal tract, the amount in the systemic circulation is below a level that would produce a significant pharmacologic effect against the drug, and therefore it is relatively inactive under these conditions.

In order to more clearly and concisely describe the subject matter of the claims, the following definitions are intended to provide guidance as to the meaning of terms used herein.

The terms "abusable drug" or "drug" as used interchangeably herein, refers to any pharmaceutically active substance or agent that has the ability to promote abuse, high tolerance with extended use, and/or chemical or physical dependency. Abusable drugs include, but are not limited to, drugs for the treatment of pain such as an opioid analgesic, e.g., and opioid or an opiate.

As used herein, the term "antagonist" refers to a moiety that renders the active agent unavailable to produce a pharmacological effect, inhibits the function of an agonist, e.g., an abusable drug, at a specific receptor, or produces an adverse pharmacological effect. For example, in some embodiments, when used in an abusive manner, the antagonist is released in an amount effective to attenuate a side effect of said opioid agonist or to produce adverse effect such as anti-analgesia, hyperalgesia, hyperexcitability, physical dependence, tolerance, or any combination thereof. Without wishing to be bound by any particular theory, it is believed that antagonists generally do not alter the chemical structure of the abusable drug itself, but rather work, at least in part, by an effect on the subject, e.g., by binding to receptors and hindering the effect of the agonist. Antagonists can compete with an agonist for a specific binding site (competitive antagonists) and/or can bind to a different binding site from the agonist, hindering the effect of the agonist via the other binding site (non-competitive antagonists). Non-limiting examples of antagonists include opioid-neutralizing antibodies; narcotic antagonists such as naloxone, naltrexone and nalmefene; dysphoric or irritating agents such as scopolamine, ketamine, atropine or mustard oils; or any combinations thereof. In one embodiment, the antagonist is naloxone or naltrexone.

The term "bioerodable" as used herein refers to the property of the devices of the present invention which allow the solid or semisolid portion of the device to sufficiently degrade by surface erosion, bioerosion, and/or bulk degradation such that it is small enough to be swallowed. Bulk degradation is the process in which a material, e.g., a polymer, degrades in a fairly uniform manner throughout the matrix. This results in a reduction of molecular weight ($M_n$) without immediate change in physical properties, followed by fragmentation due to faster penetration of saliva or water into the device than conversion of the device into saliva- or water-soluble form. Bioerosion or surface erosion generally occurs when the rate at which saliva or water penetrates the material is slower than the rate of the conversion of the material into saliva- or water-soluble substances. Bioerosion generally results in a thinning of the material over time, though the bulk integrity is maintained. It is to be understood that "bioerodable" refers to the device as a whole, and not necessarily to its individual components. For example, if the antagonist is microencapsulated or coated, the microcapsules or coating may or may not be bioerodable, but the device as a whole may be bioerodable such that as the device is eroded the intact microcapsules or coated antagonist is swallowed. This can be advantageous because the device will erode and the microcapsules or coated antagonist can be delivered to the GI tract intact, i.e., without crossing the mucosa. The term "bioerodable" is intended to encompass many modes of material removal, such as enzymatic and non-enzymatic hydrolysis, oxidation, enzymatically-assisted oxidation, wear, degradation and/or dissolution.

Bioerodable materials are generally selected on the basis of their degradation characteristics to provide a sufficient functional lifespan for the particular application. In the case of applications of the present invention, a functional lifespan of between 1 minute and 10 hours may be suitable. In some embodiments, the functional lifespan is about 2 minutes. In some embodiments, the functional lifespan is about 5 minutes. In some embodiments, the functional lifespan is about 10 minutes. In some embodiments, the functional lifespan is about 15 minutes. In some embodiments, the functional lifespan is about 20 minutes. In some embodiments, the functional lifespan is about 30 minutes. In some embodiments, the functional lifespan is about 45 minutes. In some embodiments, the functional lifespan is about 60 minutes. In some embodiments, the functional lifespan is about 2 hours. In some embodiments, the functional lifespan is about 3 hours. In some embodiments, the functional lifespan is about 4 hours. In some embodiments, the functional lifespan is about 5 hours. In some embodiments, the functional lifespan is about 10 hours. All ranges and values which fall between the ranges and values listed herein are meant to be encompassed by the present invention. For example, lifespans of between about 5 minutes and about 45 minutes, between about 6 minutes and about 53 minutes, between about 13 minutes and about 26 minutes, etc. are all encompassed herein. Shorter or longer periods may also be appropriate.

Bioerodable materials include, but are not limited to, polymers, copolymers and blends of polyanhydrides (e.g., those made using melt condensation, solution polymerization, or with the use of coupling agents, aromatic acids, aliphatic diacids, amino acids, e.g., aspartic acid and glutamic acid, and copolymers thereof); copolymers of epoxy terminated polymers with acid anhydrides; polyorthoesters; homo- and copolymers of α-hydroxy acids including lactic acid, glycolic acid, ε-caprolactone, γ-butyrolactone, and δ-valerolactone; homo- and copolymers of α-hydroxy alkanoates; polyphosphazenes; polyoxyalkylenes, e.g., where alkene is 1 to 4 carbons, as homopolymers and copolymers including graft copolymers; poly(amino acids), including pseudo poly(amino acids); polydioxanones; and copolymers of polyethylene glycol with any of the above.

As used herein, the articles "a" and "an" mean "one or more" or "at least one," unless otherwise indicated. That is, reference to any element of the present invention by the indefinite article "a" or "an" does not exclude the possibility that more than one of the element is present.

The term "abuse-resistant matrix" refers generally to a matrix with which an antagonist to an abusable drug is associated. An abuse resistant matrix is a matrix that effectively releases the antagonist when the device is used in an abusive manner (e.g., dissolved in water in an attempt to extract the drug, solubilized, opened, chewed and/or cut apart) so that, e.g., the antagonist is co-extracted and alters or blocks the effect the drug. However, when used as intended, e.g., in a non-abusive manner, the abuse-resistant matrix does not effectively release the antagonist. E.g., the antagonist instead is retained within the matrix and is delivered to the gastrointestinal tract where it is not readily absorbed such that any amount of antagonist delivered systemically through the mucosa and/or the GI tract does not significantly block or alter the effect of the drug.

When used in reference to the antagonist, the phrase "substantially transmucosally unavailable" refers to the fact that the antagonist in the compositions and devices of the present invention is available transmucosally in amounts that do not effect, or negligibly effect, the efficacy of the abusable drug when employed in a non-abusive manner. Without wishing to be bound by any particular theory, it is believed that the antagonist is prevented or slowed from entering the system transmucosally while still being available for other routes of administration (e.g., swallowing or dissolution), thus allowing the abusable drug to act efficaciously in a transmucosal composition, but hindering the use of the composition in an abusive manner. That is, it is to be understood that the antagonist effects the efficacy of the abusable drug when the compositions of the present invention are abused. In non-abusive situations, the antagonist provides no or negligible effect, e.g., is swallowed. In some embodiments, less than about 25% antagonist (by weight versus abusable drug) can be delivered non-abusively, e.g., transmucosally. In other embodiments, less than about 15% antagonist is delivered transmucosally. In still other embodiments, less than 5% of antagonist is delivered transmucosally. In some embodiments, less than 2% antagonist is delivered transmucosally. In still other embodiments, less than 1% antagonist is delivered transmucosally.

Accordingly, in some embodiments, when the device is a multilayer disc or film, the abuse-resistant matrix is a layer or is incorporated into a layer which is disposed between a mucoadhesive layer and a backing layer. In other embodiments, the abuse-resistant matrix is incorporated into a backing layer. Without wishing to be bound by any particular theory, it is believed that the antagonist would not able to enter systemic circulation through the mucosa in any significant amount because it would be washed into the GI tract, e.g., swallowed. In some embodiments, the abuse resistant matrix is a coating or water-hydrolysable matrix, e.g., an ion-exchange polymer. The coating or water-hydrolysable matrix can be chosen such that it dissolves more slowly than a backing layer as described above. The coating or water-hydrolysable matrix can additionally or alternatively be chosen such that they dissolve slowly enough not to release the antagonist at all. Without limiting the invention, it is believed that the antagonist would be washed into the GI tract as either free-antagonist or as a coated or otherwise entrapped, e.g., by the ion-exchange polymer, moiety. It is to be understood that layers, coatings, and water-hydrolyzable matrices are exemplary, and that additional abuse-resistant matrices can be envisioned using the teachings of the present invention.

As used herein, the term "abusive manner" refers to the use of the delivery device in a manner not intended, e.g., in a non-transmucosal manner or in a manner not otherwise prescribed by a physician. In some embodiments, the abusive manner includes extraction of the drug from the delivery device for oral or parenteral administration. As used herein, "non-abusive manner" refers to the use of the delivery device for its intended purpose, e.g., transmucosal administration of the drug. In some cases, a portion of the drug will unintentionally be delivered non-transmucosally, e.g., orally through the dissolution of a portion of the device. Such inadvertent or unintentional delivery is not indicative of use in an abusive manner.

Accordingly, in some embodiments, the devices of the present invention are less susceptible to abuse than an abusable drug alone. For example, when used in an abusive manner, the abusable drug may only retain about 50%, 40%, 30%, 20%, 10%, 5%, 2%, 1% or 0% of its efficacy, e.g., as a pain reliever. Accordingly, when used in an abusive manner, it is believed that the effectiveness of the abusable drug, e.g., the ability to produce a "high" in an addict, would be reduced by a corresponding amount, e.g., by 50%, 60%, 70%, 80%, 90%, 95%, 98%, 99% or 100%.

As used herein, "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder (e.g., to alleviate pain).

The term "subject" refers to living organisms such as humans, dogs, cats, and other mammals. Administration of the drugs included in the devices of the present invention can be carried out at dosages and for periods of time effective for treatment of a subject. An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation. Similarly, effective amounts of antagonist to a drug will vary according to such factors such as the amount of drug included in the devices.

In some embodiments, the antagonist and the abusable drug are incorporated into a delivery device such as the devices described in U.S. Pat. No. 5,800,832 and/or U.S. Pat. No. 6,585,997, the entireties of which are incorporated herein by this reference. In other embodiments, the antagonist and the abusable drug are incorporated into a delivery device that is dissimilar to the devices described in U.S. Pat.

No. 5,800,832 and/or U.S. Pat. No. 6,585,997. It is to be understood that any transmucosal drug delivery device can be used with the teachings of the present invention to provide an abuse-resistant device of the present invention.

In some embodiments, the antagonist and the abusable drug are incorporated into a narcotic drug product. In other embodiments, the antagonist and the abusable drug are incorporated into an antagonist drug product. In one embodiment, the antagonist drug product is a naloxone drug product.

In some embodiments, the antagonist and the abusable drug are incorporated into a delivery device such as the devices described in U.S. Pat. No. 6,200,604 (incorporated herein in its entirety by this reference) and/or U.S. Pat. No. 6,759,059 (incorporated herein in its entirety by this reference). In other embodiments, the antagonist and the abusable drug can be combined in a sublingual or buccal monolayer or multilayer tablets. In some embodiments, the antagonist and the abusable drug are incorporated into a mucoadhesive liquid and/or a mucoadhesive solid formulation. It is to be understood that any sublingual tablet, buccal tablet, mucoadhesive liquid formulation and/or mucoadhesive solid formulation can be used with the teachings of the present invention to provide an abuse-resistant device of the present invention.

In some embodiments, the antagonist and the abusable drug are incorporated into a delivery device such as a transdermal drug device, for example, a transdermal patch. In some embodiments, the transdermal drug device is a transdermal analgesic drug device. It is to be understood that any transdermal drug device can be used with the teachings of the present invention to provide an abuse-resistant device of the present invention.

In some embodiments, the abuse-resistant drug delivery device is in the form of a disc, patch, tablet, solid solution, lozenge, liquid, aerosol or spray or any other form suitable for transmucosal delivery.

As used herein, the term "incorporated" as used with respect to incorporation of a drug and/or an antagonist into the devices of the present invention or any layer of the devices of the present invention, refers to the drug or antagonist being disposed within, associated with, mixed with, or otherwise part of a transmucosal device, e.g., within one or more layers of a multilayered device or existing as a layer or coating of the device. It is to be understood that the mixture, association or combination need not be regular or homogeneous.

In some embodiments, the delivery devices of the present invention are substantially free of inactivating agents. As used herein, the term "inactivating agent" refers to a compound that inactivates or crosslinks the abusable drug, in order to decrease the abuse potential of the dosage form. Examples of inactivating agents include polymerizing agents, photoinitiators, and formalin. Examples of polymerizing agents include diisocyanates, peroxides, diimides, diols, triols, epoxides, cyanoacrylates, and UV activated monomers.

Accordingly, in some embodiments, the present invention is directed to devices and methods for treating pain in a subject, e.g., a human, with a dosage of an abusable drug while reducing the abuse potential. The methods can employ any of the devices enumerated herein with any of the desired release profiles herein, e.g., absorption of less than 10% of the antagonist through the mucosa into systemic circulation.

In the present invention, a novel device is employed for application to mucosal surfaces to provide transmucosal delivery of an abusable drug, e.g., an opioid analgesic into the systemic circulation providing rapid onset with minimal discomfort and ease of use. Accordingly, in one aspect, the devices of the present invention include an abusable drug and an antagonist to the abusable drug associated with an abuse-resistant matrix. The delivery device can be a mucoadhesive drug delivery device, a buccal delivery device, and/or a sublingual delivery device.

The devices of the present invention may include any number of layers, including but not limited to mucoadhesive layers, non-adhesive layers, backing layers and any combination thereof. In some embodiments, the device includes a mucoadhesive layer. In some embodiments, the device includes a mucoadhesive layer and a non-adhesive backing layer. In other embodiments, the device includes a third layer disposed between the mucoadhesive layer and the backing layer. In some embodiments, either or both of the abusable drug and the abuse-resistant matrix are incorporated into a mucoadhesive layer. In some embodiments, the abuse-resistant matrix is incorporated into the backing layer. In some embodiments, either or both of the abusable drug and the abuse-resistant matrix are incorporated into the third layer. In some embodiments, the abuse-resistant matrix is the third layer. Furthermore, where the device contains a third layer between the mucoadhesive layer and the backing layer, this third layer can be indistinguishable from the mucoadhesive layer. Such an embodiment can be useful because it prevents the removal of layers from the device in an effort to extract the drug. The third layer may also be co-extractable with the abusable drug. In some embodiments, the third layer is a non-adhesive layer. In some embodiments, either or both of the abusable drug and the abuse-resistant matrix are incorporated into any combination of layers discussed herein. Any or all of the layers of the transmucosal delivery device can be water-soluble.

In some embodiments, the antagonist is incorporated in the backing layer. This embodiment can be employed to allow the antagonist to release quickly in a situation when one may try to abuse the product. In this embodiment, the antagonist would be substantially swallowed upon erosion of the backing layer such that there is minimum transmucosal adsorption of the antagonist. In another embodiment, the antagonist is incorporated into a layer which is disposed between the adhesive drug layer and the backing layer. This allows delayed or sustained release of the antagonist. By separating the antagonist and the drug in separate indistinguishable layers, the antagonist does not interfere with the transmucosal delivery of the drug. In yet another embodiment, the antagonist may be commingled with the drug in the mucoadhesive layer. This aspect allow the drug and the antagonist to be physically in the same layer thus providing superior abuse resistance, in that the drug and the antagonist will be inseparable when used in an abusive manner.

In some embodiments, the abusable drug is included in a mucoadhesive layer, generally closest to the treatment site, and the backing layer protects the mucoadhesive layer from contact with saliva or other fluid resulting in slower dissolution of the mucoadhesive layer and longer contact of the mucoadhesive layer and drug with the treatment site. In such embodiments, the placement of the abusable drug in the mucoadhesive layer allows the abusable pharmaceutically active substance to unidirectionally diffuse through the buccal mucosa of the mouth and into the systemic circulation, while avoiding first pass metabolism by the liver.

The mucoadhesive layer, e.g., a bioerodible mucoadhesive layer, is generally comprised of water-soluble polymers which include, but are not limited to, hydroxyethyl cellulose, hydroxypropyl cellulose, hydroxypropylmethyl cellulose, hydroxyethylmethyl cellulose, polyacrylic acid (PAA) which may or may not be partially crosslinked, sodium carboxymethyl cellulose (NaCMC), and polyvinylpyrrolidone (PVP), or combinations thereof. Other mucoadhesive water-soluble polymers may also be used in the present invention.

The backing layer, e.g., a bioerodible non-adhesive backing layer, is generally comprised of water-soluble, film-forming pharmaceutically acceptable polymers which include, but are not limited to, hydroxyethyl cellulose, hydroxypropyl cellulose, hydroxypropylmethyl cellulose, hydroxyethylmethyl cellulose, polyvinylalcohol, polyethylene glycol, polyethylene oxide, ethylene oxide-propylene oxide co-polymers, or combinations thereof. The backing layer may comprise other water-soluble, film-forming polymers as known in the art. Exemplary mucoadhesive and non-adhesive layers, including polymers suitable for such layers are also described, e.g., in U.S. Pat. Nos. 5,800,832 and 6,159,498, the entireties of which are incorporated by this reference.

The devices of the present invention can provide, when desired, a longer residence time than those devices known in the art. In some embodiments, this is a result of the selection of the appropriate backing layer formulation, providing a slower rate of erosion of the backing layer. Thus, the non-adhesive backing layer is further modified to render controlled erodibility which can be accomplished by coating the backing layer film with a more hydrophobic polymer selected from a group of FDA approved Eudragit™ polymers, ethyl cellulose, cellulose acetate phthalate, and hydroxyl propyl methyl cellulose phthalate, that are approved for use in other pharmaceutical dosage forms. Other hydrophobic polymers may be used, alone or in combination with other hydrophobic or hydrophilic polymers, provided that the layer derived from these polymers or combination of polymers erodes in a moist environment. Dissolution characteristics may be adjusted to modify the residence time and the release profile of a drug when included in the backing layer.

In some embodiments, any of the layers in the devices of the present invention may also contain a plasticizing agent, such as propylene glycol, polyethylene glycol, or glycerin in a small amount, 0 to 15% by weight, in order to improve the "flexibility" of this layer in the mouth and to adjust the erosion rate of the device. In addition, humectants such as hyaluronic acid, glycolic acid, and other alpha hydroxyl acids can also be added to improve the "softness" and "feel" of the device. Finally, colors and opacifiers may be added to help distinguish the resulting non-adhesive backing layer from the mucoadhesive layer. Some opacifers include titanium dioxide, zinc oxide, zirconium silicate, etc.

The device according to the invention may comprise one or more opioid analgesics with potential for abuse and one or more antagonists. However, in some embodiments, the device according to the invention comprises only one active opioid analgesic and only one antagonist for this active opioid analgesic.

The abusable drug, e.g., an opioid analgesic, agonist, or partial agonist according to the invention, include, but are not limited to, alfentanil, allylprodine, alphaprodine, apomorphine, anileridine, apocodeine, benzylmorphine, bezitramide, buprenorphine, butorphanol, clonitazene, codeine, cyclorphan, cyprenorphine, desomorphine, dextromoramide, dextropropoxyphene, dezocine, diampromide, diamorphone, dihydrocodeine, dihydromorphone, dimenoxadol, eptazocine, ethylmorphine, etonitazene, etorphine, fentanyl, fencamfamine, fenethylline, hydrocodone, hydromorphone, hydroxymethylmorphinan, hydroxypethidine, isomethadone, levomethadone, levophenacylmorphan, levorphanol, lofentanil, mazindol, meperidine, metazocine, methadone, methylmorphine, modafinil, morphine, nalbuphene, necomorphine, normethadone, normorphine, opium, oxycodone, oxymorphone, pholcodine, profadol remifentanil, sufentanil, tramadol, and corresponding derivatives, and/or their physiologically acceptable compounds, in particular salts and bases, stereoisomers thereof, ethers and esters thereof, and mixtures thereof.

Pharmaceutically acceptable salts include inorganic salts and organic salts, e.g., hydrobromides, hydrochlorides, mucates, succinates, n-oxides, sulfates, malonates, acetates, phosphate dibasics, phosphate monobasics, acetate trihydrates, bi(heplafluorobutyrates), maleates, bi(methylcarbamates), bi(pentafluoropropionates), mesylates, bi(pyridine-3-carboxylates), bi(trifluoroacetates), hemitartrates, (bi)tartrates, chlorhydrates, fumarates and/or sulfate pentahydrates.

In some embodiments, the present invention includes devices having at least one opioid analgesic in a dosage range of about 1 µg to about 50 mg. In some embodiments, the present invention includes devices having at least one opioid analgesic in a dosage range of about 10 µg to about 25 mg. In still other embodiments, the devices of the present invention have at least one opioid analgesic in a dosage range of about 50 µg to about 10 mg. It is to be understood that all values and ranges between these values and ranges are meant to be encompassed by the present invention.

The amount of abusable drug to be used depends on the desired treatment strength, although preferably, the abusable drug comprises between about 0.001 and about 30% by weight of the device. It is to be understood that all values and ranges between the listed values and ranges are to be encompassed by the present invention.

The antagonist to the abusable drug can be an opioid antagonist. Opioid antagonists are known to those skilled in the art and are known to exist in various forms, e.g., as salts, bases, derivatives, or other corresponding physiologically acceptable forms. The opioid antagonists can be, but are not limited to, antagonists selected from the group consisting of naloxone, naltrexone, nalmefene, nalide, nalmexone, nalorphine, naluphine, cyclazocine, levallorphan and/or their physiologically acceptable salts, bases, stereoisomers, ethers and esters thereof and mixtures thereof.

In some embodiments, the devices of the present invention include an opioid antagonist in a dosage range of about 1 µg to about 20 mg. In some embodiments, the devices of the present invention include an opioid antagonist in a dosage range of about 1.0 µg to about 20 mg. In still other embodiments, the devices of the present invention include an opioid antagonist in a dosage range of about 10 µg and about 10 mg. It is to be understood that all values and ranges between these values and ranges are meant to be encompassed by the present invention. In some embodiments, the amount of antagonist used is such that the likelihood of abuse of the abusable drug is lessened and/or reduced without diminishing the effectiveness of the abusable drug as a pharmaceutical.

In some embodiments, the antagonist is absorbed into systemic circulation through the mucosa only to a certain desired extent. For example, in some embodiments, the extent of absorption of the antagonist is less than about 15%. In some embodiments, the extent of absorption of the antagonist is less than about 10%. In some embodiments, the extent of absorption of the antagonist is less than about 5%, 4%, 3%, 2% or 1%.

The amount of antagonist which is useful to achieve the desired result can be determined at least in part, for example, through the use of "surrogate" tests, such as a VAS scale (where the subject grades his/her perception of the effect of the dosage form) and/or via a measurement such as pupil size (measured by pupillometry). Such measurements allow one skilled in the art to determine the dose of antagonist relative to the dose of agonist which causes a diminution in the opiate effects of the agonist. Subsequently, one skilled in the art can determine the level of opioid antagonist that causes aversive effects in physically dependent subjects as well as the level of opioid antagonist that minimizes "liking scores" or opioid reinforcing properties in non-physically dependent addicts. Once these levels of antagonist are determined, it is then possible to determine the range of antagonist dosages at or below this level which would be useful in achieving the desired results.

The antagonist is associated with an abuse-resistant matrix. The abuse-resistant matrix can be, but is not limited to a layer or coating, e.g., a water-erodable coating or a water-hydrolysable matrix, e.g., an ion exchange polymer, or any combination thereof. Thus, in one embodiment of the invention, the antagonist is associated with the matrix in a manner such that it is not released in the mouth. In another embodiment of the invention, the antagonist is adequately taste masked. The entrapment and/or taste masking may be achieved by physical entrapment by methods, such as microencapsulation, or by chemical binding methods, e.g., by the use of a polymer that prevents or inhibits mucoabsorption of the antagonist, e.g., ion exchange polymers. Without wishing to be bound by any particular theory, it is believed that the optimum formulation for the particular antagonist may be determined by understanding the ratios needed to prevent abuse, evaluating the possible binding mechanism, and evaluating the physico-chemical properties of the antagonists.

In some embodiments, the antagonist is microencapsulated in an enteric polymer, polysaccharide, starch or polyacrylate. Without wishing to be bound by a particular theory, it is believed that microencapsulation will substantially prevent transmucosal absorption of the antagonist, and allow the subject to swallow the microencapsulated antagonist. The coating of the microcapsules can be designed to offer delayed release characteristics, but will release when the article or composition are placed in an aqueous environment, such as when the dosage form is chewed or subject to extraction. Delayed release can be accomplished, for example, by the use of starches or pH dependent hydrolysis polymers as coating materials for the microencapsulated antagonist. Starches, for example, would be susceptible to any enzymes that are present in the saliva, such as salivary amylase.

In some embodiments, the antagonist is microencapsulated in a microcapsule or microsphere and then incorporated in the abuse resistant matrix. Such a microcapsule or microsphere containing antagonist may be comprised of polymers such as polyacrylates, polysaccharides, starch beads, polyactate beads, or liposomes. In a further embodiment, the microspheres and microcapsules are designed to release in specific parts of the small intestine.

In another embodiment, the devices of the present invention include the antagonist in a micromatrix with complexing polymers such that the micromatrix is incorporated in the abuse resistant matrix. In yet another embodiment, the antagonist is incorporated in a slowly hydrolysable or slowly eroding polymer which is then incorporated in the abuse resistant matrix.

In some embodiments, the opioid resides in the mucoadhesive layer, which is in contact with the mucosa, while the antagonist resides in the backing layer, which is non-adhesive and erodes over time. When present, a layer disposed between the mucoadhesive layer and the backing layer may also include an antagonist. This may provide a lower driving force for the antagonist absorption in the transmucosal space, while still being swallowed upon release. The antagonist will also be released promptly from the layer disposed between the mucoadhesive layer and the backing layer, thus hindering abuse.

In one embodiment, the abuse-resistant matrix comprises water soluble polymers, e.g., polymers similar to those described for the mucoadhesive and/or backing layers, but is associated with the device such that the antagonist is not mucosally absorbed to a significant extent. For example, the matrix can be a third layer disposed between a mucoadhesive layer and a backing layer.

In one embodiment of an exemplary layered device, the drug can be placed in the mucoadhesive layer along with an antagonist which is chemically bound to a polymer, e.g., pharmaceutically acceptable ion-exchange polymer and/or which is physically entrapped in a microcapsule within a water soluble polymer coating. Upon extraction in water, both the drug and the antagonist are extracted simultaneously, eliminating the abuse potential of the extracted drug. In some embodiments, the chemical bond between the polymer, e.g., the ion-exchange polymer, and the antagonist is also hydrolysable.

In an exemplary three layered device configuration, the drug can be placed in the mucoadhesive layer, while the antagonist is placed in an indistinguishable, sandwiched third layer either in a physically or chemically bound state as described herein. Again, upon extraction in water, both the drug and its antagonist are extracted reducing or eliminating the abuse potential of the extracted drug.

In some embodiments, the abuse-resistant matrix is a water-hydrolysable matrix. The term "water-hydrolysable matrix" as used herein, refers to a controlled release matrix that allows water hydrolysis of the matrix at a desired rate, thus also effecting release of the material within the matrix at the desired rate. In some embodiments, the water-hydrolysable matrix is an ion-exchange polymer. In some embodiments, the water-hydrolysable matrix, e.g., the ion-exchange polymer is chosen such that it erodes at a rate slower than the erosion rate of the mucoadhesive layer. In other embodiments, the water-hydrolysable matrix is chosen such that it erode at a rate slower than the erosion rate of the mucoadhesive layer but quicker than the erosion rate of the non-adhesive backing layer. In some embodiments, the rate of dissociation of the antagonist from the ion-exchange polymer is slower than the rate of erosion of the layer in which it is incorporated.

In some embodiments, chemical binding of the antagonist by ion exchange polymers can also facilitate taste masking and will delay the release of the antagonist allowing the antagonist to be swallowed. Under triggered ionic change induced by ionic molecules (e.g., defined by the Hofmeister's series) or a shift in pH, the drug can be hydrolyzed from the ionic polymer.

In some embodiments, the abuse-resistant matrix includes materials used for chemical binding, e.g., in ion-exchange polymers. Such materials include, but are not limited to, polyanhydrides, poly(hydroxyethyl methacrylate), polyacrylic acid, sodium acrylate, sodium carboxymethyl cellulose, poly vinyl acetate, poly vinyl alcohols, poly(ethylene oxide), ethylene oxide-propylene oxide co-polymers, poly (N-vinyl pyrrolidone), poly(methyl methacrylate), polyacrylamide, poly(ethylene-co-vinyl acetate), poly(ethylene glycol), poly(methacrylic acid), gelatin, chitosan, collagen and derivatives, albumin, polyaminoacids and derivatives, polyphosphazenes, polysaccharides and derivatives and commercial polymers such as, but not limited to, noveon AA1 POLYCARBOPHIL™, PROVIDONE™, AMBERLITE™ IRP69, DUOLITE™ AP143, AMBERLITE™ IRP64, and AMBERLITE™ IRP88, and any combinations thereof. A cationic polymer such as AMBERLITE™ IR-122 or an anion exchange resin such as AMBERLITE™ IRA-900 may also be used, depending upon the pKa of the drug. Functional groups may include, but are not limited to R—$CH_2N^+$($CH_3$)$_3$, R—$CH_2N^+$($CH_3$)$_2C_2H_4OH$, R—$SO_3$—, R—$CH_2N^+H(CH_3)_2$, R—$CH_2COO$—, R—COO—, and R—$CH_2N(CH_2COO)_2$.

The selection of the ion exchange polymer depends on the pKa of the antagonist, and functional groups attached to the drug moiety such as —COOH, —OH or amine functionalities on its backbone which could be used to bind to an ion exchange polymer. The amount of the drug loaded on to the ion exchange polymer depends on the molecular weight of the opioid antagonist, the type of ion exchange polymer used, and its ionic stoichiometric ratio. In some embodiments, the antagonist to ion exchange polymer ratios range from about 1:99 to about 99:1. In other embodiments, the antagonist to ion exchange polymer ratios range from about 1:9 to about 9:1. In other embodiments, the antagonist to ion exchange polymer ratios range from about 1:3 to about 3:1.

In some embodiments, the abuse-resistant matrix is a layer coating, e.g., a water-erodable coating. That is, physical entrapment of the antagonist in the device, e.g., the mucoadhesive layer, can be facilitated by a barrier layer which is coated with a water soluble polymer which erodes slowly. That is, antagonists may be at least partially coated or disposed within water-erodable coating. Methods of microencapsulation and particle coating have been defined in the literature.

In some embodiments, the abuse-resistant matrix includes materials used for physical entrapment. Such materials include, but are not limited to, alginates, polyethylene oxide, poly ethylene glycols, polylactide, polyglycolide, lactide-glycolide copolymers, poly-epsilon-caprolactone, polyorthoesters, polyanhydrides and derivatives, methyl cellulose, ethyl cellulose, hydroxypropyl cellulose, hydroxyethyl cellulose, hydroxyethylmethyl cellulose, hydroxypropylmethyl cellulose, polyacrylic acid, and sodium carboxymethyl cellulose, poly vinyl acetate, poly vinyl alcohols, polyethylene glycol, polyethylene oxide, ethylene oxide-propylene oxide co-polymers, collagen and derivatives, gelatin, albumin, polyaminoacids and derivatives, polyphosphazenes, polysaccharides and derivatives, chitin, chitosan bioadhesive polymers, polyacrylic acid, polyvinyl pyrrolidone, sodium carboxymethyl cellulose and combinations thereof.

Other exemplary water-erodable coatings and water-hydrolysable matrices are known in the art, e.g., in U.S. Pat. Nos. 6,228,863 and 5,324,351.

In some embodiments, the device provides an appropriate residence time for effective opioid analgesic delivery at the treatment site, given the control of solubilization in aqueous solution or bodily fluids such as saliva, and the slow, natural dissolution of the film concomitant to the delivery. The residence time can also be tailored to provide a range from minutes to hours, dependent upon the type of opioid used and therapeutic indication. In some embodiments, residence times of between about 20 to 30 minutes and about 3 to 4 hours are achieved with the devices of the present invention.

In other embodiments, residence times of between about 1 hour and about 2 hours are achieved. The residence time of the device of the present invention depends on the dissolution rate of the water-soluble polymers used. The dissolution rate may be adjusted by mixing together chemically different hydrophilic and hydrophobic polymers or by using different molecular weight grades of the same polymer. Such adjustments are well described in the art of controlled release.

As the materials used in the devices of the present invention are soluble in water, illicit use efforts to extract the opioid from the adhesive layer for parenteral injection, are thwarted by the co-extraction of the opioid antagonist. The amount of opioid antagonist contained in the product is designed to block any psychopharmacological effects that would be expected from parenteral administration of the opioid alone.

In some embodiments, upon use of the device in an abusive manner, the antagonist is generally released (e.g., dissolved in water or some other appropriate solvent) at substantially the same rate as the abusable drug. For example, in some embodiments, the antagonist to the abusable drug is released at substantially the same time as the opioid when abusively dissolved. As used herein, the term "abusively dissolved" refers to dissolution in a solvent other than saliva, for example, water, ethanol or the like. In other embodiments, the antagonist is released at a slower rate as the abusable drug when abusively dissolved. In such cases, the amount of antagonist released would be sufficient to hinder the use of the abusable drug, e.g., by producing unwanted side effects. In some embodiments, the released antagonist to opioid ratio is not less than 1:20. In other embodiments, the released antagonist to opioid ratio is not less than 1:10. In still other embodiments, the released antagonist to opioid ratio is not less than 1:5. In yet other embodiments, the released antagonist to opioid ratio is at least about 1:10. In yet other embodiments, the released antagonist to opioid ratio is at least about 1:20. In yet other embodiments, the released antagonist to opioid ratio is at least about 1:50. Any values and ranges between the listed values are intended to be encompassed by the present invention.

If desired, flavoring agents known in the art may be added to mask the taste of the active compound. Penetration enhancers may also be included in the adhesive layer to help reduce the resistance of the mucosa to drug transport. Typical enhancers known in the art include ethylenediamine tetracetic acid, chitosan, etc. Ingredients to enhance drug solubility and/or stability of the drug may also be added to the layer or layers containing the abusable drug. Examples of stabilizing and solubilizing agents are cyclodextrins.

In some embodiments, the devices and methods of the present invention further include one or more drugs in addition to the abusable drug and antagonist. In some embodiments, a combination of two abusable drugs may be included in the formulation. Two such drugs may, e.g., have different properties, such as half-life, solubility, potency, etc. Additional drugs can provide additional analgesia, and include, but are not limited to, aspirin; acetaminophen; non-steriodial antiinflammatory drugs ("NSAIDS"), N-methyl-D-aspartate receptor antagonists, cycooxygenase-II inhibitors and/or glycine receptor antagonists. Such additional drugs may or may not act synergistically with the opioid analgesic. Further drugs include antiallergic compounds, antianginal agents, anti-inflammatory analgesic agents, steroidal anti-inflammatory agents, antihistamines, local anesthetics, bactericides and disinfectants, vasoconstrictors, hemostatics, chemotherapeutic drugs, antibiotics, keratolytics, cauterizing agents, hormones, growth hormones, growth hormone inhibitors, analgesic narcotics and antiviral drugs.

In one aspect, the present invention includes methods for treating pain in a subject. The method can include administering any of the devices described herein such that pain is treated.

The pharmaceutical delivery device of the present invention may be prepared by various methods known in the art. For example, in one embodiment, the components are dissolved in the appropriate solvent or combination of solvents to prepare a solution. Solvents for use in the present invention may comprise water, methanol, ethanol, or lower alkyl alcohols such as isopropyl alcohol, acetone, ethyl acetate, tetrahydrofuran, dimethyl sulfoxide, or dichloromethane, or any combination thereof. The residual solvent content in the dried, multilayered film may act as a plasticizer, an erosion- or dissolution-rate-modifying agent or may provide some pharmaceutical benefit. Desired residual solvent may reside in either or both layers.

Each solution is then coated onto a substrate. Each solution is cast and processed into a thin film by techniques known in the art, such as film coating, film casting, spin coating, or spraying using the appropriate substrate. The thin film is then dried. The drying step can be accomplished in any type of oven. However, the solvent residual depends on the drying procedure. The film layers may be filmed independently and then laminated together or may be filmed one on the top of the other. The film obtained after the layers have been laminated together or coated on top of each other may be cut into any type of shape, for application to the mucosal tissue. Some shapes include disks, ellipses, squares, rectangles, and parallepipedes.

EXEMPLIFICATION

Example 1

Effect of Naloxone on Efficacy of Fentanyl

The purpose of this study is to determine the dose range over which IV naloxone administered in combination with IV fentanyl, would precipitate opioid withdrawal signs and symptoms and attenuate any pleasurable effects from intravenous injection in subjects with a moderate level of opioid dependence. It is believed that the addition of this ratio of naloxone to a transmucosal formulation of fentanyl would hinder or prevent abuse.

The trial was a randomized, double-blind, placebo controlled, within-subject crossover study in opioid-dependent volunteers. Subjects were maintained on methadone prior to inpatient admission and throughout the 9-day study period. Subjects received each of the 5 study doses and evaluated the psychopharmacologic effects of each.

The subjects included males or non-pregnant and non-lactating females; 18 to 55 years of age; free from any significant clinical abnormalities on the basis of medical history and physical examination, ECG, and screening laboratory tests; weighing at least 50 kg (110 lbs); with an opioid positive urine sample (>300 ng/ml) and an alcohol-free breath sample (<0.002%).

Subjects were not eligible for the study if they exhibited certain indications or illnesses. For example, subjects with certain psychiatric illness, neurological disease, cardiovascular disease, pulmonary disease, systemic disease, were ineligible. Additionally, subjects with alcohol or sedative abuse and/or dependence, subjects who were cognitively impaired, subjects concurrently being treated for opioid dependence with methadone, buprenorphine, LAAM, or naltrexone, subjects on any medication other than oral or depot contraceptives and subjects with an injection phobia were excluded from the study. Furthermore, women candidates who were pregnant, lactating, or heterosexually active not using medically approved birth control measures were not eligible.

Opioid-dependent males and females, ages 18 to 55 years, were recruited. Volunteers were not concurrently seeking treatment for their drug use, and were willing to participate in a short-term study involving methadone maintenance and detoxification, and a consecutive 8-night (9-day) inpatient stay with experimental sessions involving intravenous drug administrations. Each subject who was eligible to participate in the study was assigned a study number.

A complete medical and drug history was taken and a complete physical examination was performed on each subject, including a measurement of height and weight. Respiration rate, oxygen saturation, heart rate, and blood pressure were measured during all test sessions using a Welch Allyn Noninvasive Patient Monitor. Vital signs including respiration rate, heart rate, systolic and diastolic blood pressure and oxygen saturation were measured prior to each dose and at 5, 10, 15, 30, 45 and 60 minutes after each dose. Each subject's oxyhemoglobin saturation was closely monitored. If the subject's oxyhemoglobin saturation remained below 90% for more than 1 minute, oxygen was administered to the subject via a nasal cannula, an adverse event was documented and the subject was monitored. Subjects requiring oxygen administration were excluded from further study participation. A 12-lead electrocardiogram was obtained for each subject at screening. Females of childbearing potential had a urine pregnancy test performed according to the study schedule. A positive result at any time during the study excluded the subject from participating in the trial. All adverse events were recorded.

The laboratory tests listed in the following table were obtained according to the study schedule for each subject. All clinically significant laboratory abnormal values were specifically noted.

| HEMATOLOGY | BLOOD CHEMISTRY | OTHER |
| --- | --- | --- |
| Hemoglobin | Sodium | Urinalysis |
| Hematocrit | Potassium | Urine drug screen |
| Platelet Count | Chloride | Urinary beta-HCG |
| RBC Count | Bicarbonate | (females only) |
| White Blood Cell Count Differential, including: | Calcium Phosphorus (inorganic) Glucose | |
| Neutrophils | Urea Nitrogen | |
| Lymphocytes | Creatinine | |
| Monocytes | Uric Acid | |
| Eosinophils | Cholesterol | |
| Basophils | Bilirubin (total) Protein (total) Albumin SGOT (AST) SGPT (ALT) Alkaline Phosphatase | |

A Mantoux/PPD tuberculosis skin test was administered into the epidermis of the inner forearm of the subjects and the site of injection was marked. Forty-eight to 72 hours after the test was administered, the test results were read to determine if the test site was raised and felt hard to the touch. Subjects with a positive PPD test were referred to the community health program (CHP) to receive a chest X-ray. If the X-ray was positive (definition of having tuberculosis), the subject was informed and referred for treatment.

Subjects were asked to complete certain questionnaires, for example, an Injection Phobia Questionnaire, questions regarding the Shipley Institute of Living Scale (used to derive IQ), an Opioid Symptom Questionnaire, a Visual analog scale (VAS) rating of subjective drug effect, questions regarding a Drug reinforcing value (e.g., to make independent choices between drug and money), and an observer-rated withdrawal assessment Treatment All experimental doses were administered by intravenous injection in a double-blind manner. The starting IV fentanyl dose was 0.6 mg (600 µg) in combination with 0.15, 0.3 and 0.6 mg naloxone. This fentanyl dose corresponded to an intermediate-sized transmucosal formulation of fentanyl, thereby providing a reasonable test of a potentially abusable dose. Depending on the initial results, the fentanyl was adjusted either upward (to a maximum of 0.8 mg) or downward (to a minimum of 0.2 mg). If dose adjustments were made, the naloxone dose was adjusted according to the following ratios: (1) placebo, (2) fentanyl≤0.8 mg+naloxone placebo, (3) fentanyl ≤0.8 mg+naloxone at 25% of the dose of fentanyl, (4), fentanyl≤0.8 mg+naloxone at 50% of the dose of fentanyl, and (5) fentanyl≤0.8 mg+naloxone at 100% of the dose of fentanyl.

Subjects were maintained on a target dose of methadone for 10 days prior to the first experimental session. Subjects also received methadone maintenance (50 mg daily) on days without experimental procedures.

Beginning on the first day of the study period and continuing each day, subjects received one of the 5 study treatments by intravenous injection at the same time each day. The timeline below indicates the times at which drug was administered and assessments were performed.

| | Time | | | | | | |
|---|---|---|---|---|---|---|---|
| | −30 min (0930) | 0 min (1000) | +5 min (1005) | +15 min (1015) | +30 min (1030) | +45 min (1045) | +60 min (1100) |
| IV drug | | x | | | | | |
| Observer | x | | x | x | x | | |
| Vitals | x | | x | x | x | x | x |
| VAS | x | | x | x | x | x | x |
| OSQ | x | | x | x | x | x | x |
| MCP | | | | | | | x |

Prior to the subjects' discharge on the last day, an evaluation of adverse events, a complete physical examination, laboratory tests and administration of first methadone detoxification dose are all performed.

Results from initial subjects are shown in FIG. 1. As can be seen in FIG. 1, there was no positive or negative effects from the placebo, there was only a positive effect from the fentanyl alone, there was no positive and some significant negative effects with fentanyl plus 25% naloxone, and there was major negative effects with fentanyl plus 50% naloxone.

Example 2

Extraction of Fentanyl and Naloxone in Water and Ethanol

A 3.11 cm$^2$ bilayered transmucosal disc was placed in 100 mL of 0.1N HCl and 0.1N NaOH. The disc was allowed to dissolve over a period of 30 minutes, and the amount of naloxone was measured using a high performance liquid chromatography. At 30 minutes, 100% naloxone and 100% fentanyl was extracted under acidic conditions, while 15% naloxone and 2% fentanyl was measured at a pH 12. The remaining amount was expected to settle at the bottom of the flask with other insoluble excipients. A 3.11 cm$^2$ bilayered transmucosal disc as described herein was placed in 100 mL of ethanol. HPLC results show both naloxone and fentanyl present.

Example 3

Extraction of Buprenorphine and Naloxone in an Aqueous Solvent

A 2.3 cm$^2$ disc containing buprenorphine in the mucoadhesive layer and naloxone in the backing layer was prepared and placed in pH 7.4 Phosphate buffered solution in a Van Henkel USP dissolution apparatus at 50 RPM. The result of the dissolution experiment is shown in the table below.

| Number of Minutes in Aqueous Solvent | Buprenorphine | Naloxone |
|---|---|---|
| 5 | 18.0% | 20.3% |
| 15 | 38.5% | 48.0% |
| 30 | 60.5% | 72.1% |
| 45 | 84.1% | 83.2% |
| 60 | 100.2% | 86.2% |
| 75 | 106.7% | 86.2% |
| 120 | 108.9% | 85.8% |
| 180 | 109.4% | 87.4% |

As can be seen in the table, naloxone and buprenorphine extract simultaneously up to 180 minutes. Thus, they can not be extracted separately via dissolution.

The invention claimed is:

1. A bioerodable abuse-resistant transmucosal drug delivery device comprising:
    an abusable drug incorporated into a mucoadhesive layer; and
    an antagonist to the abusable drug incorporated into an abuse-resistant matrix such that the antagonist is substantially transmucosally unavailable,
    wherein the abuse-resistant transmucosal drug delivery device is bioerodable.

2. The delivery device of claim 1, wherein the device is a mucoadhesive drug delivery device.

3. The delivery device of claim 1, wherein either or both of the abusable drug and the abuse-resistant matrix are incorporated into the mucoadhesive layer.

4. The drug delivery device of claim 1, comprising a non-adhesive backing layer.

5. The delivery device of claim 4, wherein the abusable drug is incorporated into a third layer disposed between the mucoadhesive layer and the backing layer.

6. The delivery device of claim 4, wherein the abuse-resistant matrix is incorporated into a third layer disposed between the mucoadhesive layer and the backing layer.

7. The delivery device of claim 4, wherein the abuse-resistant matrix is a third layer disposed between the mucoadhesive layer and the backing layer.

8. The delivery device of claim 4, wherein the abuse-resistant matrix is incorporated into the mucoadhesive layer and/or the backing layer.

9. The delivery device of claim 4, wherein the abuse-resistant matrix is incorporated into the backing layer.

10. The delivery device of claim 5, wherein the abuse-resistant matrix erodes at a slower rate than the backing layer, the mucoadhesive layer, the third layer, or any combination thereof.

11. The delivery device according to claim 1, wherein the abusable drug is selected from the group consisting of opiates and opioids.

12. The delivery device according to claim 1, wherein the device comprises at least one abusable drug selected from the group consisting of: alfentanil, allylprodine, alphaprodine, apomorphine, anileridine, apocodeine, benzylmorphine, bezitramide, buprenorphine, butorphanol, clonitazene, codeine, cyclorphan, cyprenorphine, desomorphine, dextromoramide, dextropropoxyphene, dezocine, diampromide, diamorphone, dihydrocodeine, dihydromorphine, dimenoxadol, eptazocine, ethylmorphine, etonitazene, etorphine, fentanyl, fencamfamine, fenethylline, hydrocodone, hydromorphone, hydroxymethylmorphinan, hydroxypethidine, isomethadone, levomethadone, levophenacylmorphan, levorphanol, lofentanil, mazindol, meperidine, metazocine, methadone, methylmorphine, modafinil, morphine, nalbuphene, necomorphine, normethadone, normorphine, opium, oxycodone, oxymorphone, pholcodine, profadol remifentanil, sufentanil, tramadol, corresponding derivatives, physiologically acceptable compounds, salts and bases.

13. The delivery device according to claim 1, wherein the antagonist comprises at least one opiate or opioid antagonist selected from the group consisting of naloxone, naltrexone, nalmefene, nalide, nalmexone, nalorphine, naluphine, cyclazocine, levallorphan and physiologically acceptable salts and solvates thereof.

14. The abuse-resistant drug delivery device of claim 1, wherein the antagonist and the abusable drug are released at substantially the same rate when abusively dissolved.

15. The abuse-resistant drug delivery device of claim 1, wherein the antagonist and the abusable drug are released at substantially the same rate when dissolved in water.

16. The abuse-resistant drug delivery device of claim 14, wherein the ratio of released antagonist to released abusable drug is not less than about 1:20.

17. A method for treating pain in a subject comprising administering a device according to any of the preceding claims such that pain is treated.

18. The method of claim 17, wherein the extent of the absorption into systemic circulation of the antagonist by the subject is less than about 15% by weight.

19. The method of claim 17, wherein the dosage of the abusable drug is between about 50 μg and about 10 mg.

20. A bioerodable abuse-resistant drug delivery device comprising:
   a layered film having
      at least one bioerodable, mucoadhesive layer to be placed in contact with a mucosal surface, and
      at least one bioerodable non-adhesive backing layer,
      wherein at least one abusable drug is incorporated in at least the mucoadhesive layer, and an abuse-resistant matrix comprising an antagonist to the abusable drug is incorporated in any or all of the layers such that the antagonist is substantially transmucosally unavailable.

21. The device of claim 1, wherein the device is adapted for a residence time of between about 20 minutes and about 4 hours.

* * * * *